United States Patent
Farnsworth et al.

(10) Patent No.: US 6,277,644 B1
(45) Date of Patent: Aug. 21, 2001

(54) METHOD FOR COMPOSITIONAL TAG SEQUENCING

(75) Inventors: Vincent R. Farnsworth, Agoura; Paul K. Cartier, III, Arcadia, both of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/273,945

(22) Filed: Mar. 22, 1999

(51) Int. Cl.$^7$ .................................................. G01N 33/68
(52) U.S. Cl. .............................. 436/89; 436/86; 436/808; 422/68.1; 422/83; 422/88
(58) Field of Search ................................ 436/86, 89, 808; 422/68.1, 83, 88

(56) References Cited

U.S. PATENT DOCUMENTS

| | | | |
|---|---|---|---|
| 3,645,689 | | 2/1972 | Sjoquist ............................. 23/230 R |
| 3,717,436 | * | 2/1973 | Penhasi et al. ........................ 436/89 |
| 3,725,010 | * | 4/1973 | Penhasi ................................. 422/64 |
| 3,892,531 | * | 7/1975 | Gilbert ................................ 422/116 |
| 4,065,412 | * | 12/1977 | Dreyer ................................ 525/54.1 |
| 5,059,540 | | 10/1991 | Bailey ................................. 436/89 |
| 5,082,788 | * | 1/1992 | Farnsworth et al. ................... 436/89 |
| 5,156,809 | * | 10/1992 | Hupe et al. ............................ 422/64 |
| 5,185,266 | * | 2/1993 | Boyd et al. ............................ 436/89 |
| 5,223,435 | * | 6/1993 | Kohr .................................... 436/89 |
| 5,270,213 | * | 12/1993 | Farnsworth ............................ 436/89 |
| 5,439,650 | * | 8/1995 | Tsugita et al. ....................... 422/108 |
| 5,674,743 | * | 10/1997 | Ulmer ............................... 435/287.2 |

OTHER PUBLICATIONS

A. A. Gooley, et al., A Role for Edman Degradation in Proteome Studies, Electrophoresis, 18, 1068–1072 (1997).
M. R. Wilkins, et al., From Proteins to Proteomes: Large Scale Protein Identification by Two–Dimensional Electrophoresis and Amino Acid Analysis, Bio/Technology, 14, 61–65 (1996).
V. Farnsworth et al., The Generation of Phenylthiocarbamyl or Anilinothiazolinone Amino Acids from the Postcleavage Products of the Edman Degradation, Analytical Biochemistry 215, 200–210 (1993).
P. Edman et al., A Protein Sequenator, European J. Biochem. 1, 80–91 (1967).
S. Katsui, et al., Short Communications, Biochem. J. (9165) 97, 25–26c.
Glycosite Protein Sequencer Operations Manual, p. 1–11.

* cited by examiner

Primary Examiner—Jill Warden
Assistant Examiner—Monique T. Cole
(74) Attorney, Agent, or Firm—William H. May; Arnold Grant

(57) ABSTRACT

A modified Edman degradation process is used to obtain compositional tags for proteins. The Edman degradation chemistry is separated from amino acid analysis, circumventing the serial requirement of the conventional Edman process. Multiple cycles of coupling and cleavage are performed prior to extraction and compositional analysis of amino acids. The amino acid composition information is used to search a database of known protein or DNA sequences to identify the sample protein.

16 Claims, 2 Drawing Sheets

METHOD FOR COMPOSITIONAL TAG SEQUENCING

BACKGROUND

Figure 1:
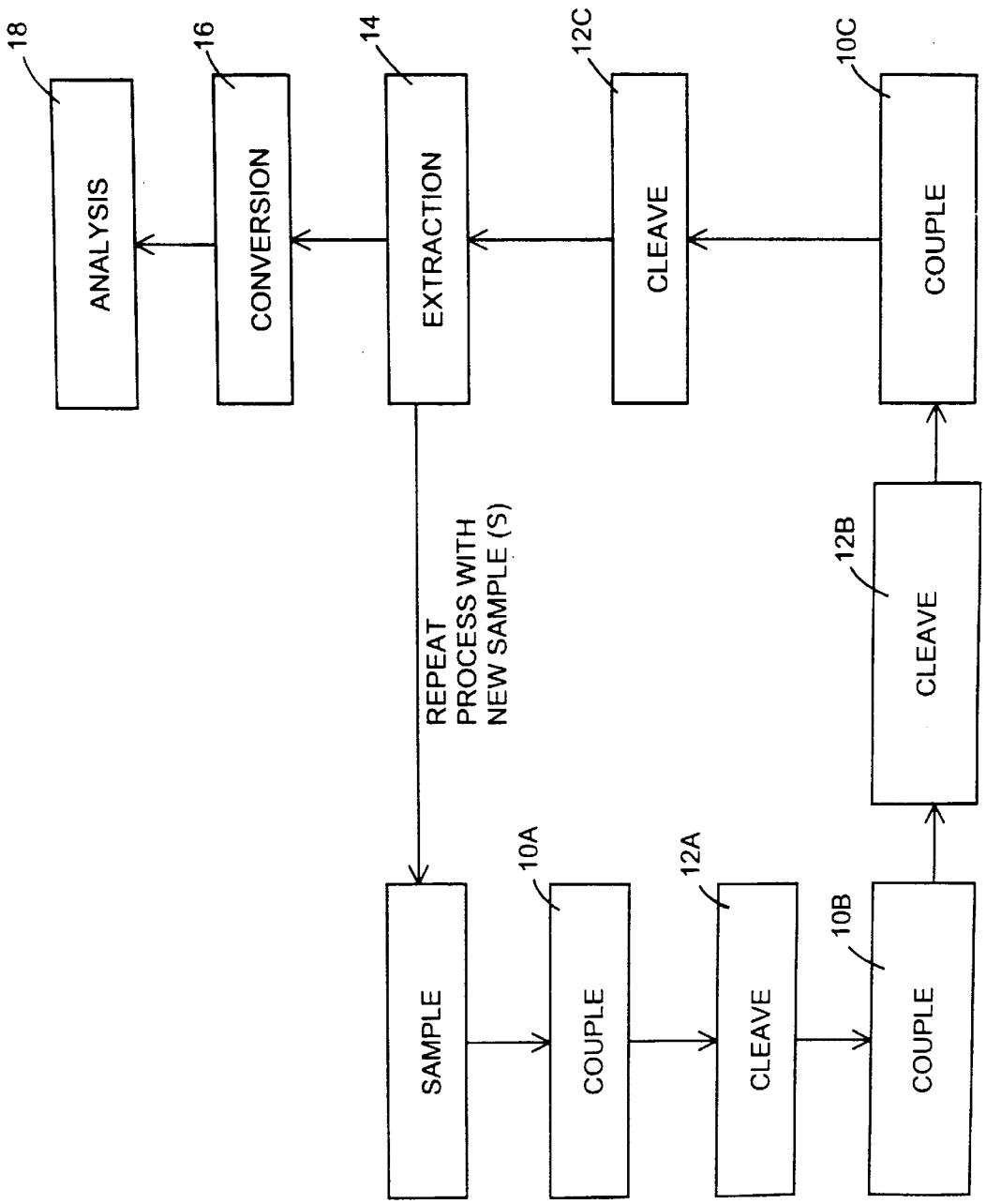

The invention relates generally to protein characterization and identification, and more specifically to an improved method and apparatus for determining the amino acid composition of a portion of a protein.

This and a related process and processing assembly are described in co-pending patent applications entitled "Protein Sequencing and Identification System", Ser. No. 09/274, 036, by Vincent Robert Farnsworth and Paul K. Cartier and "Multiple-Sample Cartridge Assembly for Automated Process", Ser. No. 09/274,559, by Vincent Robert Farnsworth, both of which applications are filed on the same day as the present application, and both of which are incorporated herein by reference.

The identification and characterization of proteins is important to correlate particular proteins with disease states and to understand the biological function of proteins. Moreover, with the Human Genome project, there is an increasing need to link newly identified genes with their functional counterparts. Various methods have been described to do this, including, for example, digesting the protein with a specific enzyme such as trypsin and then use a mass spectrometer to analyze the resulting peptide mixture. The protein is identified by comparing the experimental mass profiles, including peptide fragmentation patterns, to the predicted profiles of known proteins stored in the databases.

An alternative approach to identifying a particular protein is two-dimensional polyacrylamide gel electrophoresis. Proteins from the 2D PAGE gel are analyzed, for example by Edman degradation. The Edman degradation process involves the sequential degradation of the N-terminus of a protein or polypeptide which comprises three basic stages: coupling, cleavage, and conversion. See Edman and Begg, "A Protein Sequenator", European Journal of Biochem. 1 (1967) 80–91. The amino acids released from the Edman degradation reactions are then analyzed to determine a partial amino acid sequence, the results of which are correlated with sequence data in the existing DNA and protein databases. Unfortunately, identification of proteins by Edman degradation based sequencing is slow due to the serial nature of the process, which requires each cleaved amino acid to be analyzed prior to proceeding with the next.

These methods are of limited utility, in part because they are slow and expensive. Moreover, only one sample at a time is normally analyzed. What is needed is a way to identify proteins more rapidly and allow multiple samples to be processed in parallel.

SUMMARY

The present invention provides a system that satisfies the need, by providing a method and apparatus for determining the amino acid composition of at least a portion of at least one protein and using that information to identify the protein from a database of known sequences. The method involves coupling at least one protein with a coupling agent at one terminus of the protein so that a derivative of the amino acid at the terminus is formed, cleaving the coupled terminal amino acid from the protein such that a new amino acid is exposed at the terminus, repeating these steps of coupling and cleavage at least two times before simultaneously extracting the cleaved amino acids, identifying the extracted amino acids, determining the amino acid composition of at least a portion of the protein, and identifying the protein by comparing the amino acid composition against the amino acid compositions of a portion of known proteins.

One embodiment of the invention is a modification of the Edman degradation process which allows multiple cycles of coupling and cleavage to be performed without the normally required intervening steps of amino acid extraction and analysis. The invention enables the Edman degradation chemistry to be separated from amino acid analysis, and allows multiple cycles of coupling and cleavage to be performed prior to amino acid extractions. Preferably, the coupling and cleavage cycles are performed three or four times before the amino acids are extracted, converted, and subjected to compositional analysis. The amino acid composition information is then used to search a database of known protein or DNA sequences to identify the sample protein.

An apparatus for performing this method comprises a sample holder for holding the sample, a coupling agent supplier for supplying at least one coupling agent, a cleavage agent supplier for supplying a cleavage agent, a controller for directing the sequential supply of the coupling agents, cleavage agents, and other reagents necessary for performing the modified Edman degradation reactions, and an analyzer for analyzing amino acids.

DRAWINGS

Figure 2:
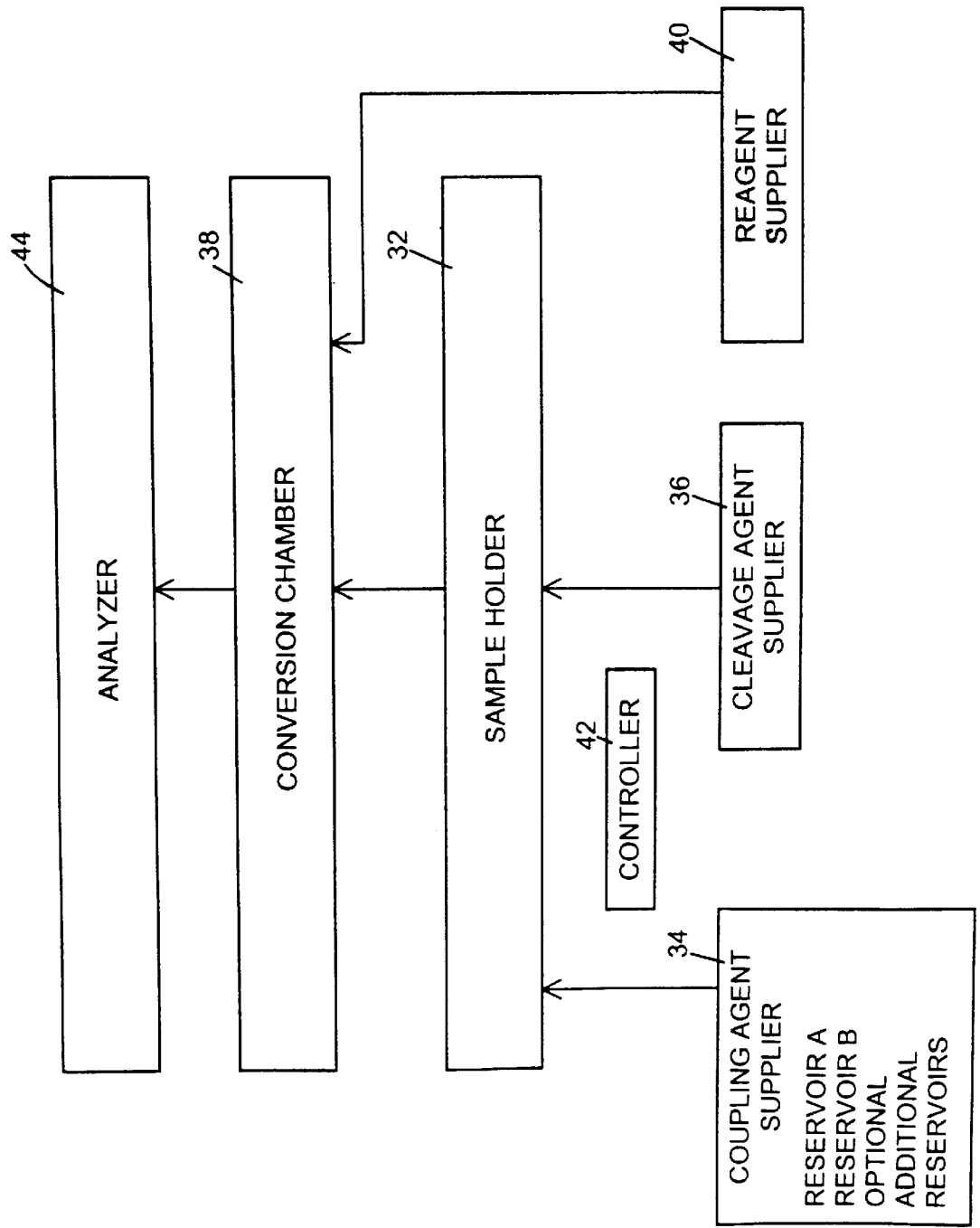

These features, aspects and advantages of the present invention will become better understood with regard to the following description, appended claims and accompanying drawings, where:

FIG. 1 is a schematic illustrating an embodiment of the invention where three cycles of coupling and cleavage are performed before the amino acid derivatives are extracted and analyzed for compositional analysis; and FIG. 2 schematically shows an apparatus for practicing the present invention.

DESCRIPTION

The invention is directed to the identification and characterization of proteins through an improved method and apparatus for determining the amino acid composition of one terminus of the protein. The invention may be applied by determining the amino acid composition of either the N-terminus or the C-terminus of a protein.

Sample

The sample is contained within a sample holder. Preferably, the sample is immobilized on a solid support and the reagents are passed over the immobilized sample. In a preferred embodiment, multiple samples are immobilized individually on their own thin substrate and are physically separated in a cartridge to prevent mixing between samples, as described in the aforementioned patent application entitled "Multiple-Sample Cartridge Assembly for Automated Processes." Each sample is preferably a substantially homogeneous protein species that has been obtained through standard protein purification procedures, including, for example, two-dimensional polyacrylamide gel electrophoresis (2D-PAGE).

Coupling and Cleavage

With reference to FIG. 1, there is shown the steps of a process according to the present invention. The process comprises a coupling step 10, a cleavage step 12, an extraction step 14, a conversion step 16, and an analysis step 18. As shown in FIG. 1, the process has coupling step 10A, cleavage step 12A, coupling step 10B, cleavage step 12B, coupling step 10C, and cleavage step 12C, in that order.

Preferably, the coupling step 10 and the cleavage step 12 are repeated at least two times, and as shown in FIG. 1, at least three times, before the extraction step 14 and the conversion step 16. The analysis step 18 includes the determination of the composition of amino acids within a short segment of the protein, which will hereinafter be referred to as a "compositional tag".

The process is generally performed by first reacting at least one coupling agent with one terminus of a protein, either the N-terminus or the C-terminus, in the coupling step 10. A preferred embodiment of the present invention comprises a modification of the Edman degradation process of the N-terminus of a protein. The conventional Edman degradation process generally involves sequential coupling, cleavage, and conversion. Edman degradation can be performed on the N-terminus of a protein, or the protein can be cleaved into peptides in which case the Edman degradation is performed from the N-terminus of peptides. In the coupling reaction, the conventional Edman process utilizes phenylisothiocyanate (PITC) distributed in an appropriate solvent as a coupling agent. The phenylisothiocyanate (PITC) reacts with the N-terminal amino group of the peptide (or protein) to form a phenylthiolcarbamyl (PTC) derivative . In the cleavage step 12, an acid induces cyclization and chain cleavage at the first amide bond of the PTC derivative to form an anilinothiazolinone (ATZ amino acid) along with a residual peptide having a new amino acid at the N-terminal position. In the final reaction, the ATZ amino acid is converted to a phenylthiohydantion (PTH) amino acid that is subjected to analysis.

In a preferred embodiment, the invention comprises a modification of the Edman process which allows multiple cycles of the coupling step 10 and the cleavage step 12 to be performed without the normally required intervening steps of amino acid extraction and analysis. Sequencing a protein by Edman degradation normally requires that each amino acid be analyzed before another cycle of coupling and cleavage is performed. This obligatory serial analysis is a rate limiting factor in conventional Edman degradation sequencing. The invention allows the Edman degradation chemistry to be separated from amino acid analysis.

In a preferred embodiment, the coupling step 10 and the cleavage step 12 are performed at least two times, and more preferably at least three or four times, on at least one protein sample before the amino acids are extracted in the extraction step 14, converted in the conversion step 16, and subjected to an analysis step 18, which includes compositional analysis. A smaller or larger number of cycles of the coupling step 10 and the cleavage step 12 can be performed prior to the extraction step 14, the conversion step 16, and the analysis step 18. Preferably, the coupling agent used in the coupling step 10 is phenylisothiocyanate (PITC). In alternative embodiments utilizing a modified Edman degradation process, coupling agents other than phenylisothiocyanate (PITC), or more than one coupling agent, can be used. Preferably, isothiocyanate analogues in which different R groups are attached to the isothiocyanate moiety are used in conjunction with Edman degradation reactions; however, still different coupling agents may be used.

In another embodiment of the invention, coupling agents which react with the C-terminus of the protein are used in degradation reactions at the C-terminus of a protein. Various C-terminal sequencing reactions described in the prior art may be used.

A preferred method for performing C-terminal sequencing utilizes diphenylphosphorylisothiocyanate (DPP-ITC) in pyridine to form a polypeptide thiohydantion derivative at the C-terminus. The derivatized amino acid is released from the polypeptide by treatment with potassium trimethylsilanolate. The amino acid derivative released is called a thiohydantion, which is sufficiently stable to be used in analysis without a conversion reaction. See Bailey, J. M. "Techniques in Protein Chemistry VI", Crabb, J. W., ed. (Academic Press, San Diego, Calif.); and Ward, C. W., "Practical Protein Chemistry-A Handbook (Darbre, A. ed) (1986). Each of the foregoing publications are herein incorporated by reference.

Gas Phase Delivery of Reagents

Preferably, the coupling agent is delivered as a gas phase. The term gas phase includes a gas containing a vaporized liquid. It is generally not harmful to deliver to a liquid coupling agent on the first cycle or solvent wash after the delivery of the first coupling agent. However, gas phase delivery of the coupling agent at subsequent cycles prevents unwanted extraction of the first cleaved amino acid derivative, and thus maximizes the amount of amino acid derivative available for analysis. Gas phase delivery of coupling agents also eliminates the need to dry the sample after application of a coupling agent in a liquid solvent and also tends to lower the amount of reaction byproducts and artifacts that can result when a liquid carrier is not of the highest purity. In an alternative embodiment of the invention, utilizing two or more different coupling agents, the different coupling agents may be supplied in a variety of ways utilizing a combination of gas phase delivery and liquid delivery.

Extraction

As illustrated in the embodiment in FIG. 1, the amino acid derivatives formed after three cycles of cleavage and coupling are extracted from the sample together in the extraction step 14. This is effected with an appropriate solvent such as ethyl acetate. The second coupling reaction is performed in a reaction mixture in which the first cleaved amino acid derivative is present because it has not yet been extracted. By separating the Edman degradation reactions from the analysis steps, multiple proteins may be subjected to Edman degradation simultaneously while deferring amino acid compositional analysis of each individual sample to a latter time. In alternative embodiments where four or more cycles of coupling and cleavage are performed, the cleaved amino acid derivatives are preferably extracted together after the last desired cleavage.

Conversion

Preferably, in the conversion step 16, the cleaved amino acid derivatives are converted to a more s table analyte before being subjected to analysis. Where phenylisothiocyanate (PITC) is used as a coupling agent, the released anilinothiazolinone (ATZ) amino acid may, for example, be converted to a phenylthiohydantion (PTH), a phenylthiocarbamyl (PTC), or a phenylthiocarbamyl amino-fluorescene (PTC-AF). Where naphtylisothiocyanate (NITC) is the coupling agent, the released aminonaphthylthiazolinone amino acid may, for example, be converted to a naphtylthiohydantion (NTH) amino acid, a naphthythiocarbamyl (NTC), or a naphtylthiocarbamyl amino-fluorescence (NTC-AF).

Analysis

After the desired number of cycles of Edman degradation are performed, the cleaved amino acids are identified by conventional analytical techniques such as high performance liquid chromatography (HPLC) or mass spectrometric (MS) analysis in the analysis step 18. The compositional amino acid analysis can be performed in a single HPLC procedure, as opposed to multiple HPLC analysis which are normally required for sequence analysis of conventional Edman degradations. The remainder of the protein sample can be subjected to further analysis, for example analysis of total amino acid composition by acid hydrolysis followed by amino acid analysis.

With Edman degradation based sequencing the amino acid derivatives normally have to be analyzed serially before subjecting the sample to another cycle of cleavage, coupling, and conversion. The invention circumvents the requirement of serial analysis by simultaneously analyzing multiple amino acid derivatives to obtain a compositional tag. The term simultaneously should not be construed as imposing a rigid time requirement for identification of amino acids, but is to be understood as within the confines of the same analytical procedure rather than serially after the completion of each cycle of the Edman process. This eliminates the need for real time analysis of the amino acid derivatives as the Edman degradation process proceeds. Thus, parallel processing of multiple protein samples is made possible because the samples may be compositionally tagged simultaneously and then analyzed individually.

Compositional Tagging and Protein Identification

The identity of the amino acids determined within a short stretch of the sample protein, rather than the sequential order of amino acids, is used to assign a compositional tag. A search program such as TagIdent is used to search a database of known protein or DNA sequences such as the SWISS-PROT database to identify the polypeptide from the compositional tag information (available on the Internet at http://expasy.hcuge.ch/sprot/tagident.html). See "The SWISS PROT protein sequence data bank and its supplement TrEMBL in 1998", Nucleic Acids Res. 26:38–42 (1998); "A role for Edman degradation in proteome studies", Electrophoresis 18:1068–1072 (1997); and "From proteins to proteomes: Large scale protein identification by two-dimensional electrophoresis and amino acid analysis", Biotechnology 14: 61–65 (1998). Each of the foregoing publications are herein incorporated by reference.

The TagIdent search program allows the sequence database to be searched for a compositional tag. Essentially the program searches a protein or DNA sequence database for all possible sequence permutations and gives a ranked list of proteins that closely match the criteria entered. In a preferred embodiment, a compositional tag from the N-terminus of the protein sample is used to search a database of known DNA or protein sequences in order to identify the protein sample. In an alternative embodiment, a compositional tag from the C-terminus of a protein is used to search a protein or DNA sequence database. In still another preferred embodiment of the invention, the compositional tag information is used in conjunction with other information, including but not limited to, the apparent protein mass, the PI, or the total amino acid composition of the protein to identify the protein within a database of known DNA or protein sequences.

Instrumentation

With reference to FIG. 2, an apparatus for sequencing a polypeptide sample generally has a sample holder 32 for placement in a reaction chamber. The sample holder 32 preferably has a support for immobilizing the sample. More preferably, the support is removably mounted in a cartridge wherein multiple samples are capable of being immobilized individually on their own thin substrate and physically separated. The apparatus has at least one coupling agent supplier 34 for supplying at least one coupling agent in the form of a liquid, a gas, or a vaporized liquid to the sample within the sample holder 32.

The apparatus has a separate cleavage agent supplier 36 for supplying a cleavage agent to the sample and a conversion chamber 38 in which the amino acid conversion reactions occur. The apparatus may also have at least one reagent supplier 40 for delivering other such as conversion reagents and solvents. The apparatus also has a controller 42 for directing the sequential supply of the coupling agents, cleavage agents, and other reagents necessary for performing the polypeptide sequencing reactions described herein. The controller 42 can be a computer or other analogous electronic device. The apparatus has an analyzer 44 for analyzing amino acids, amino acid derivatives, polypeptides, and proteins. Analysis of the amino acids can be integrated with the apparatus performing the Edman degradation reactions, for example in an analytical module attached to an instrument performing the sequencing reactions, or may be performed off-line on a separate instrument. The analytical methods performed by the analyzer 44 include, but are not limited to, mass spectrometry, HPLC, and computer based analysis. The apparatus for performing the modified Edman reactions can be any prior art protein sequencer that has been appropriately configured to perform at least three cycles of coupling and cleavage prior to amino acid extractions and analysis. An apparatus that is capable of being successfully modified to perform the protein sequencing steps is the Beckman LF 3600 protein sequencer, sold by Beckman-Coulter of Fullerton, Calif.

EXAMPLE

The compositional tagging method was tested on an undigested α-lactalbumin sample. A Beckman LF 3600 protein sequencer was configured to deliver the Edman coupling reagent in the gas phase. The sequencer was loaded with ten 100 picomole samples of α-lactalbumin on Beckman Hyperbond membrane strips. A special ten-sample reaction cartridge was used. This cartridge is described in the aforementioned patent application entitled "Multiple-Sample Cartridge Assembly for Automated Processes." Samples to be tagged were dissolved in 10% acetonitrile and spotted onto Hyperbond strips that had been prewetted with methanol. The strips were dried at 65° C. and then loaded into the sample cartridge. The samples were tagged for three Edman cycles using gaseous phenyl isothiocyanate. Gas-phase coupling was effected by bubbling nitrogen through a 30% solution of PITC in heptane. The LF 3600 was set up for gas-phase delivery from the R1 (30% PITC) and S3 (TFA) reservoirs. The pressurization and delivery lines were reversed in the R1 and S3 reservoirs so that the pressure line extended to the bottom of the bottle and the delivery line was above the surface of the liquid. Flow rates were adjusted to 30 cc/minute for R1 and 3.8 cc/minute for S3.

Six of the ten samples were chosen at random for amino acid analysis. The latent amino acids from each of the six strips were extracted, converted to PTH and analyzed separately. The amino acid derivatives were identified by HPLC. Chromatography was performed on the LF 3600 HPLC module using Beckman solvents. Solvent A was 0.016M ammonium formate at pH 4.0 and solvent B was acetonitrile. The column was a Beckman 2.1×250 mm C-18 with 3$\mu$ packing maintained at 50° C. Flow rate was 0.2 ml/minute. A linear gradient from 12 to 30% solvent B in 0.4 minutes, 30–40% in one minute, 40–52% in two minutes, 52–55% in one minute and 55–60% in 0.5 minute performed the separation. The column was washed with 80% solvent B for two minutes before returning to 12% B for reequilibration. Detection was at 268 nm.

All six samples showed essentially the same amino acid composition, which was glutamic acid, glutamine and leucine. This composition matched that expected for the first three amino acids found in α-lactalbumin. The mean yields for each of these amino acids in the six samples was 54.9 picomoles (glutamic acid), 47 picomoles (glutamine) and 23.6 picomoles (leucine).

Although the present invention has been described in considerable detail with reference to certain preferred versions thereof, other versions are possible. For example, C-terminal compositional tags may derived from C-terminal degradation reactions. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. A method for determining the amino acid composition of at least a portion of at least one protein comprising:
   a) coupling at least one protein with a coupling agent at one terminus of the protein such that a derivative of the amino acid at the terminus is formed;
   b) after (a), cleaving the coupled terminal amino acid from the protein such that a new amino acid is exposed at the terminus;
   c) repeating (a) and (b) at least one more time without extracting the cleaved amino acids;
   d) after (c), extracting the cleaved amino acids simultaneously; and
   e) identifying the extracted amino acids simultaneously.

2. The method of claim 1 wherein (a) and (b) are performed two times before extracting.

3. The method of claim 1 wherein (a) and (b) are performed three times before extracting.

4. The method of claim 1 wherein coupling the protein with the coupling agent is performed at the N-terminus of the protein.

5. The method of claim 1 wherein (a) to (d) are performed on at least two proteins simultaneously.

6. The method of claim 1 wherein the coupling agent is delivered in a gas phase.

7. A method for identifying proteins comprising:
   a) coupling at least one protein with a coupling agent at one terminus of the protein such that a derivative of the amino acid at the terminus is formed;
   b) after (a), cleaving the coupled terminal amino acid from the protein such that a new amino acid is exposed at the terminus;
   c) repeating (a) and (b) at least two times without extracting the cleaved amino acids;
   d) after (c), extracting the cleaved amino acids simultaneously;
   e) after (d), identifying the extracted amino acids;
   f) determining the amino acid composition of at least a portion of the protein; and
   g) identifying the protein by comparing the amino acid composition of at least a portion of the protein against the amino acid compositions of a portion of known proteins.

8. The method of claim 7 wherein (a) and (b) are performed two times before extracting.

9. The method of claim 7 wherein (a) and (b) are performed three times before extracting.

10. The method of claim 7 wherein coupling the protein with the coupling agent is performed at the N-terminus of the protein.

11. The method of claim 7 wherein (a) to (g) are performed on at least two proteins simultaneously.

12. The method of claim 7 wherein the coupling agent is delivered as a gas phase.

13. A method for determining the composition of at least a portion of a protein comprising:
   a) coupling the protein with a first coupling agent at one terminus of the such that a derivative of the amino acid at the terminus is formed;
   b) after (a), cleaving the coupled terminal amino acid from the protein such that a new amino acid is exposed at the one terminus;
   c) after (b), without extracting the cleaved amino acid, coupling the protein with a second coupling agent at the one terminus;
   d) after (c), cleaving the coupled amino acid from the protein;
   e) extracting the cleaved amino acids simultaneously; and
   f) identifying the extracted amino acids.

14. The method of claim 12 wherein the first coupling agent is the same as the second coupling agent.

15. The method of claim 12 wherein the first coupling agent and the second coupling agent are different.

16. An apparatus for determining the amino acid composition of at least a portion of a protein, the apparatus comprising
   a) a reaction chamber;
   b) a sample holder for holding the sample in the reaction chamber;
   c) a coupling agent supplier for supplying a coupling agent to the reaction chamber;
   d) a cleaving agent supplier for supplying a cleaving agent to the reaction chamber;
   e) an analyzer for analyzing cleaved amino acids; and
   f) a controller for sequentially:
      (i) supplying the coupling agent from the coupling agent supplier to the reaction chamber;
      (ii) supplying the cleavage agent from the cleavage agent supplier to the reaction chamber for cleaving the coupled terminal amino acid from the sample;
      (iii) repeating (i) and (ii) at least one more time;
      (iv) after (iii), extracting the cleaved amino acids from the reaction chamber; and
      (v) identifying the cleaved amino acids in the analyzer.

* * * * *